United States Patent [19]
Johns et al.

[11] Patent Number: 5,618,556
[45] Date of Patent: Apr. 8, 1997

[54] DRESSINGS

[75] Inventors: Owen L. Johns, Madeira Beach; Peter J. Metcalfe, St. Petersburg, both of Fla.

[73] Assignee: Smith & Nephew United Inc, Largo, Fla.

[21] Appl. No.: 579,922

[22] Filed: Dec. 28, 1995

Related U.S. Application Data

[63] Continuation of Ser. No. 216,581, Mar. 23, 1994, abandoned.

[51] Int. Cl.$^6$ ..................................................... A61F 13/00
[52] U.S. Cl. ........................... 424/448; 424/443; 602/46; 602/58
[58] Field of Search .................................. 424/443, 448; 602/46, 58

[56] References Cited

U.S. PATENT DOCUMENTS

| | | | |
|---|---|---|---|
| Re. 33,727 | 10/1991 | Sims | 128/851 |
| 4,753,232 | 6/1988 | Ward | 602/52 |
| 4,910,020 | 3/1990 | Samour | 424/448 |

FOREIGN PATENT DOCUMENTS 0360458  3/1990  European Pat. Off. .

*Primary Examiner*—D. Gabrielle Phelan
*Attorney, Agent, or Firm*—Larson and Taylor

[57] ABSTRACT

There is described an adhesive dressing comprising a backing layer having a pressure sensitive adhesive layer over one surface thereof, a pad adhered to a portion of the adhesive layer a removable protector which covers the remainder of the adhesive layer and a conformable support layer which is lightly attached to the non-adhesive surface of the backing layer characterised in that the removable protector is provided with an aperture through which the pad is adhered to the adhesive layer.

15 Claims, 4 Drawing Sheets

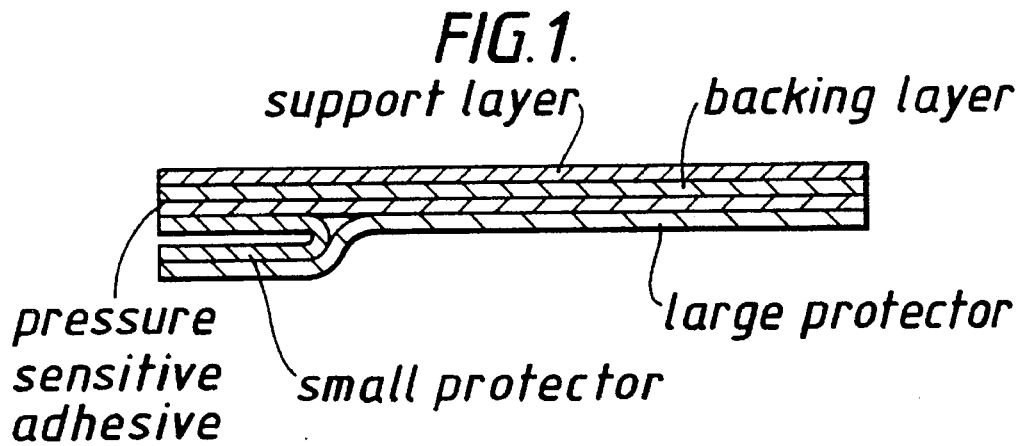
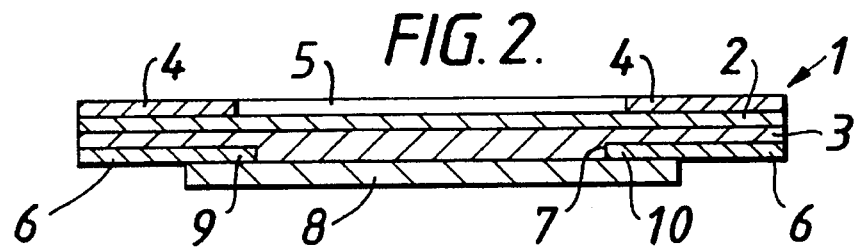
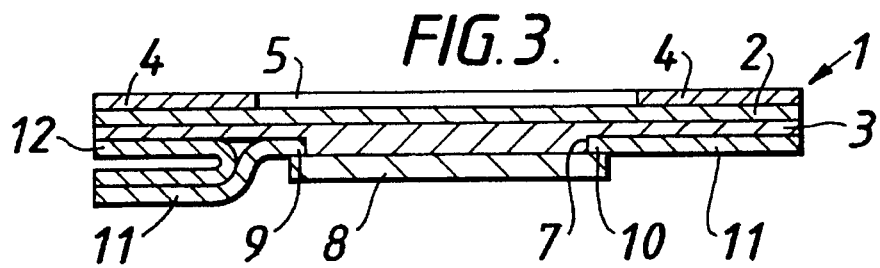
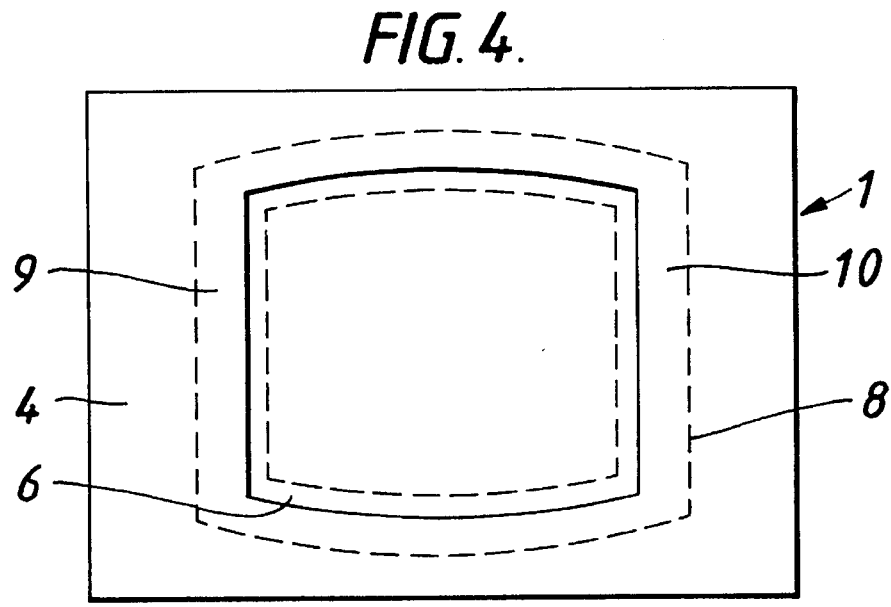

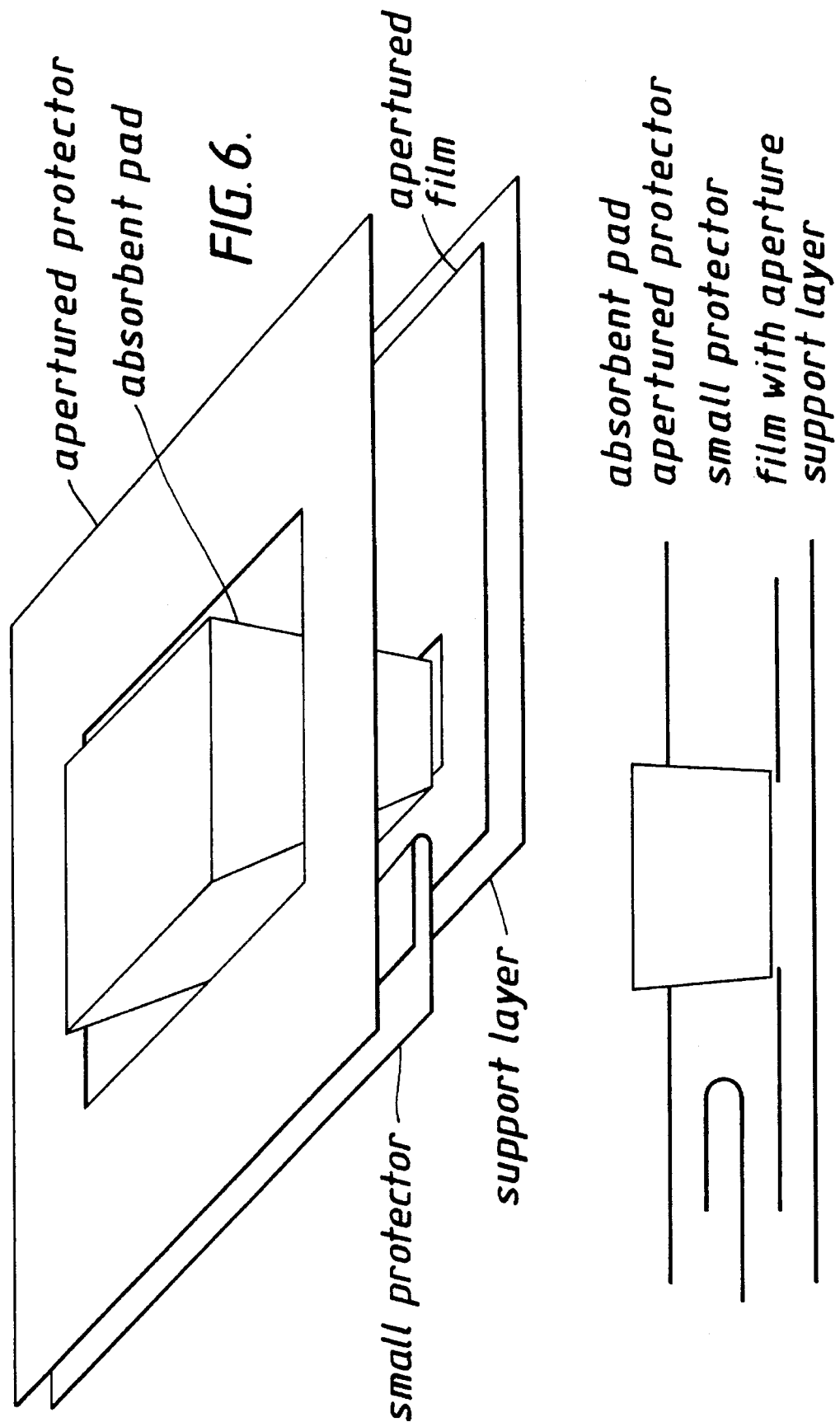

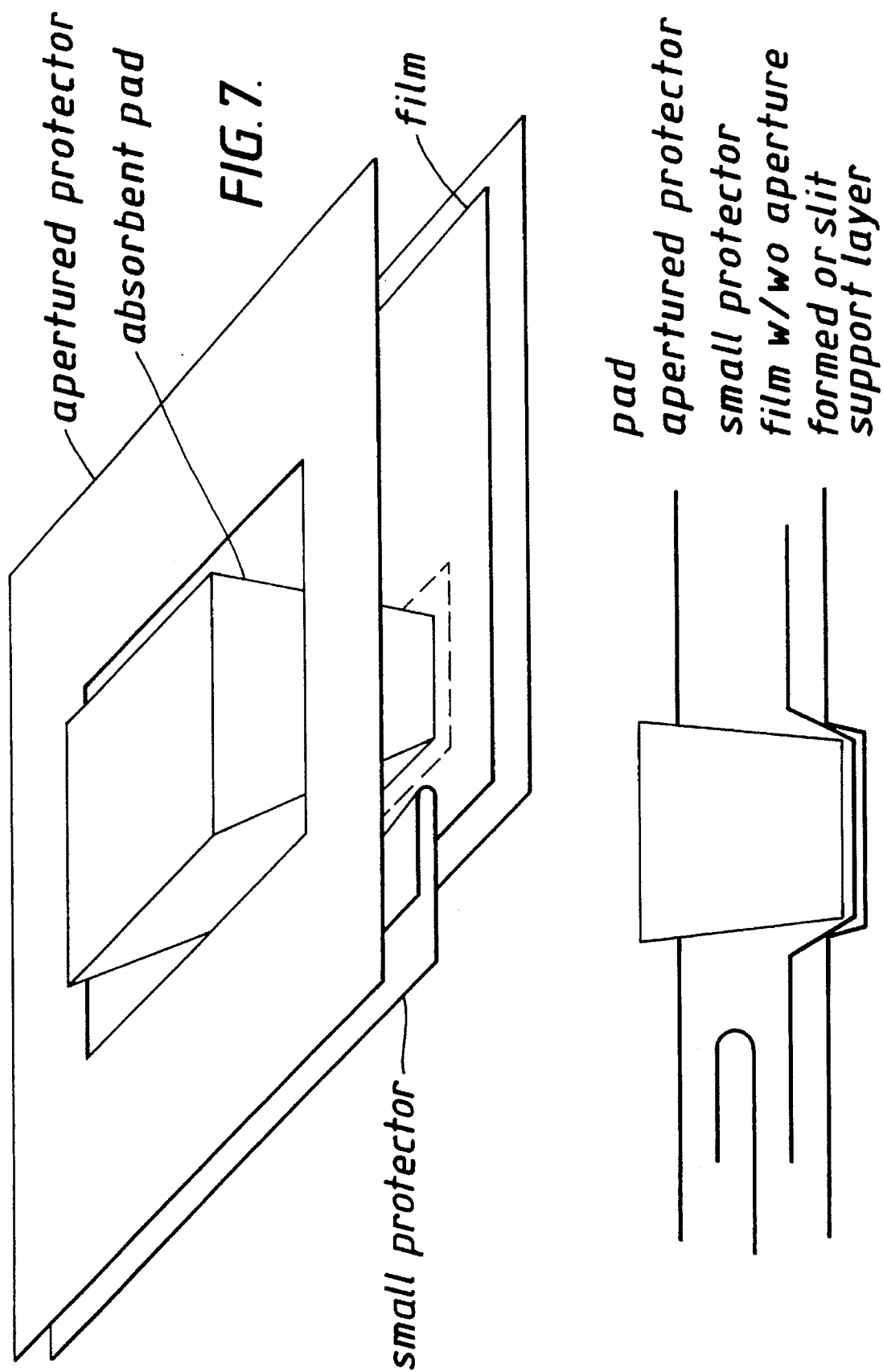

DRESSINGS

This application is a continuation of application Ser. No. 08/216,581 filed Mar. 23, 1994, now abandoned.

This invention relates to a novel form of dressing and a novel method of treatment of wounds.

It is often desirable, in the treatment of large wound areas, to apply a dressing comprising a pad provided with a water vapour permeable, liquid water and bacteria impermeable adhesive coated backing. However, such dressings suffer from the disadvantage that, unless they are handled with extreme care, excessive wrinkling occurs, which may prevent or hinder the dressing from adhering to the area on or around the wound.

One method of overcoming this problem is described in U.S. Pat. No. RE 33727. U.S. '727 describes the application of a dressing by use of an attached and detachable frame. However, this system is costly, requiring the use of an additional rigid frame and consequently it is also relatively cumbersome to package and to apply.

However, we have now found an adaptation of a dressing product known as OPSITE FLEXIGRID™ which comprises a pad and an adhesive coated backing layer wherein the backing layer is provided with an apertured protector through which the pad is able to contact with the adhesive layer. The apertured protector provides sufficient rigidity to the dressing to avoid undesirable wrinkling, but also facilitates the provision of uniform protection for the adhesive coated backing layer. OPSITE FLEXIGRID™ dressings are described in European Patent No. 360458.

According to the invention we provide an adhesive dressing comprising a backing layer having a pressure sensitive adhesive layer over one surface thereof, a pad adhered to a portion of the adhesive layer, a removable protector which covers the remainder of the adhesive layer and a conformable support layer, which is lightly attached to the non-adhesive surface of the backing layer said removable protector being provided with an aperture through which the pad is adhered to the adhesive layer.

The aperture in the removable protector may be greater than or the same size as the surface of the pad. However, we prefer the size of the aperture to be less than the surface of the pad such that the pad partially overlies the outer surface of the protector, thus allowing the pad to adhere to the recently exposed adhesive once the protector is removed. The extent to which the pad overlaps the surface of the protector may vary but is preferably up 25% of the width of the pad, more preferably up 15%, especially up to 10%, eg. 5 to 10%.

Suitably the backing layer is a thin film and may comprise any of those materials which are conventionally employed to form thin film surgical dressing. Suitable materials include those described in UK Patent No. 1280631. European Patents Nos. 51935, 91800 and 178740. Particularly apt materials are polyurethanes, for example polyester or polyether polyurethanes known as Estanes (Trade Mark). Other apt materials are elastomeric polyether polyesters, for example those known as Hytrels (Trade Mark) and polyether polyamides, for example those known as Pebaxes (Trade Mark). Other favoured materials include hydrophilic polymers such as hydrophilic polyurethanes including those described in UK Patent No. 2093190B, especially the polyurethane described in Example 2 therein. Such materials will typically take up from 5 to 95% by weight of water.

The materials employed in the dressings of the invention may be moisture vapour permeable. The moisture vapour transmission rate of the materials employed in the present invention may be measured by a procedure known as the Payne Cup method, which method is described in European Patent Application No. 360458. The method uses a cup 1.5 cm deep with a flanged top. The inner diameter of the flange is such to provide an area for moisture vapour transmission of 10 cm$^2$. In this method 10 ml of chilled water is added to the cup and a sample of the material under test, large enough to completely cover the flange, is clamped over the cup. The complete assembly is then weighed and placed in a cabinet where the temperature and relative humidity are maintained at 37° C. and 10% respectively. After 17 hours the cup is removed from the cabinet and allowed to cool at room temperature. After re-weighing, the mass of water lost by vapour transmission is calculated and the result expressed in gm$^{-2}$ 24 hrs$^{-1}$ at 37° C. at 100% to 10% relative humidity difference.

The backing layer may be moisture vapour permeable and may have a moisture vapour transmission rate of at least 500 gm$^{-2}$ 24 hrs$^{-1}$ relative humidity difference, more suitably at least 1200 gm$^{-2}$ 24 hrs$^{-1}$ and preferably at least 1600 gm$^{-2}$ 24 hrs$^{-1}$.

The backing layer may have a thickness of from 15 to 100 μm, preferably 20 to 80 μm and more preferably 25 to 50 μm, for example 27.5μ, 30 μm, 35 μm, 40 μm.

The pressure sensitive adhesive layer may be formed from an adhesive which is conventionally used for contact with the skin. Suitable adhesives include polyvinyl alkyl ether adhesive and acrylate ester copolymer adhesives. Suitable adhesives are described in UK Patent No. 1280631 and European Patents Nos. 35399 and 51935. Preferably the adhesive is a polyvinyl ether adhesive or an acrylate ester copolymer adhesive formed by the polymerisation of 2-ethylhexyl acrylate, butyl acrylate and acrylic acid.

The adhesive layer may be from 15 to 65 μm thick, for example 20 to 40 μm thick and is applied at a weight per unit area of 10 to 75 gsm, more suitably 15 to 65 gsm and preferably 25 to 40 gsm.

The backing and adhesive layers may have one or more openings to expose the absorbent pad if greater MVTR is required.

The pad may be comprised of foam, eg. a polyurethane foam, gauze, hydrocolloids, absorptive granules and/or layers and combinations of these materials. Other materials or combinations of materials used for absorbing body fluids would also be suitable.

Since the pad will generally be placed on the adhesive layer through the aperture in the protector layer, if the aperture in the removable protector is less than the size of the pad, said pad will only be loosely adhered at its peripherary until the protector is removed.

The removable protector is preferably a silicone coated release paper. Suitably the removable protector may have a weight per unit area of 100 to 140 gsm, and preferably 110 to 130 gsm, for example 120 gsm. The removable protector maybe divided into two or more pieces or fenestrated to facilitate removal. Preferably at least one of the protector pieces is significantly larger than the other or others and covers a major proportion of the adhesive layer. It is desirable that the stripping load of the support layer from the backing layer is greater than that of the protector from the adhesive layer otherwise there is a risk that the support layer would peel from the backing layer before the protector can be removed.

The support layer may be any suitable conformable material, thus suitable materials include paper, foil or polymeric films. Preferably the support layer is a polymeric film.

Suitable polymeric films are disclosed in UK Patent No. 2219211. The support layer may be opaque. Preferably the support layer is transparent. The support layer may be adhesively bonded to the backing layer using any suitable adhesive. The adhesive should have a peeling strength such that on removal of the support layer from the backing layer, the backing layer is not dislodged from the skin. Thus the peeling strength of the adhesive on the skin-facing surface of the backing layer should be greater than the peeling strength of the adhesive on the non-skin-facing surface of the backing layer. The support layer may comprise reference marks as disclosed in GB2219211. Thus for example, the reference marks may indicate dimensions, eg. 20 cm, 35 cm, etc.

In a preferred embodiment of the present invention, the conformable material comprises a support layer which is non-adhesively bonded to the backing layer. A suitable method of non-adhesively bonding the support layer to the backing layer is disclosed in GB2219211.

The support layer may have a greater surface area than the surface area of the backing layer. Thus the support layer may have one or more edge portions which extend beyond the backing layer. Where such edge portions are present they may be used as handles for gripping to aid removal of the support layer. Preferably the edges of the support layer are co-terminous with the edges of the backing layer.

It is a further feature of this invention to provide an adhesive dressing as hereinbefore described wherein the removable protector extends beyond the backing layer at one or more edges and comprises first and second parts, the first parts having a portion extending away from the adhesive surface and bent back to form a v-shape and the second part having a portion extending away from the adhesive and overlying the v-shaped first part.

The support layer preferably extends beyond the backing layer on one or more sides to allow easy removal after the adhesive layer is attached.

In a further feature of the invention the conformable support layer is formed or, preferably, slit. The provision of these features facilitates the application of the dressing whilst removing the conformable support layer.

The adhesive dressing may be prepared by casting a solution of the polymer which is to form the backing layer onto a long strip of the film which is to form the support layer. An adhesive may be cast or transfer coated onto the backing layer. The backing layer and adhesive layer may then be trimmed shorter than the support layer. The removable protector may then be applied to the adhesive surface in one or two pieces as described hereinbefore. The pad is then applied to the exposed adhesive layer. The material so formed may be further trimmed and then cut transversely to form dressings of the appropriate size. The dressings may have an area equivalent to 5×5 cm to 20×20 cm, for example 5×7.5 cm, 10×12 cm.

The adhesive dressing may be placed in a bacteria-proof pack, sealed and sterilised by conventional methods including using ethylene oxide or irradiation.

In use the sterile adhesive dressing is removed from the pack, the removable protector is removed, the adhesive layer is applied to the skin of the patient and the support layer may then be removed since the edges extend beyond the adhesive coated backing layer and are thus easily grasped by the fingertips.

In another aspect therefore the present invention provides a method of treating a wound or indwelling catheter site which comprises applying thereto an adhesive dressing as hereinbefore described by removing the removable protector, applying the adhesive layer to the skin and then removing the support layer by an edge extending beyond the backing layer.

BRIEF DESCRIPTION OF THE DRAWINGS

Preferred embodiments of adhesive dressings of the present invention will now be described by way of example only and with reference to the accompanying drawings, in which FIG. 1 is a cross section through one embodiment of a dressing according to the prior art, FIG. 2 is a cross section through one embodiment of the present invention, FIG. 3 is a cross-section through a further embodiment of the present invention in which a handle is attached, FIG. 4 is a plan view of the embodiment of FIG. 2, FIG. 6 is a schematic representation of a dressing according to the invention in which the backing layer or film is apertured, and FIG. 7 is a schematic representation of a dressing according to the invention in which the backing layer or film is formed or slit.

FIG. 2 shows an adhesive dressing (1) which comprises a backing layer (2) formed from a film of polyether polyurethane. The backing layer (2) has on one surface a pressure sensitive adhesive layer (3) formed from polyacrylate ester adhesive. On the non-adhesive surface of the backing layer (2) is a support layer (4) which may be slit or formed. The support layer (4) may comprise a silicone or polyethylene coated paper or a transparent film of polyethylene or polypropylene and extends beyond one or more edges (2). The adhesive layer (3) is provided with a protector (6) preferably made from a silicone coated release paper. The protector (6) is provided with an aperture (7) through which a pad (8) is adhered to the adhesive layer (3). The dimensions of the pad (8) are such that it overlaps the edges (9,10) of the aperture (7) thus preventing any contact of the adhesive with the environment and consequent risks of contamination.

FIG. 3 shows a further embodiment of the invention in which the protector (6) comprises two components. The larger protector (11) is essentially flat and overlaps the smaller protector (12), and the smaller protector (12) is folded into a v-shape.

Figure 5:
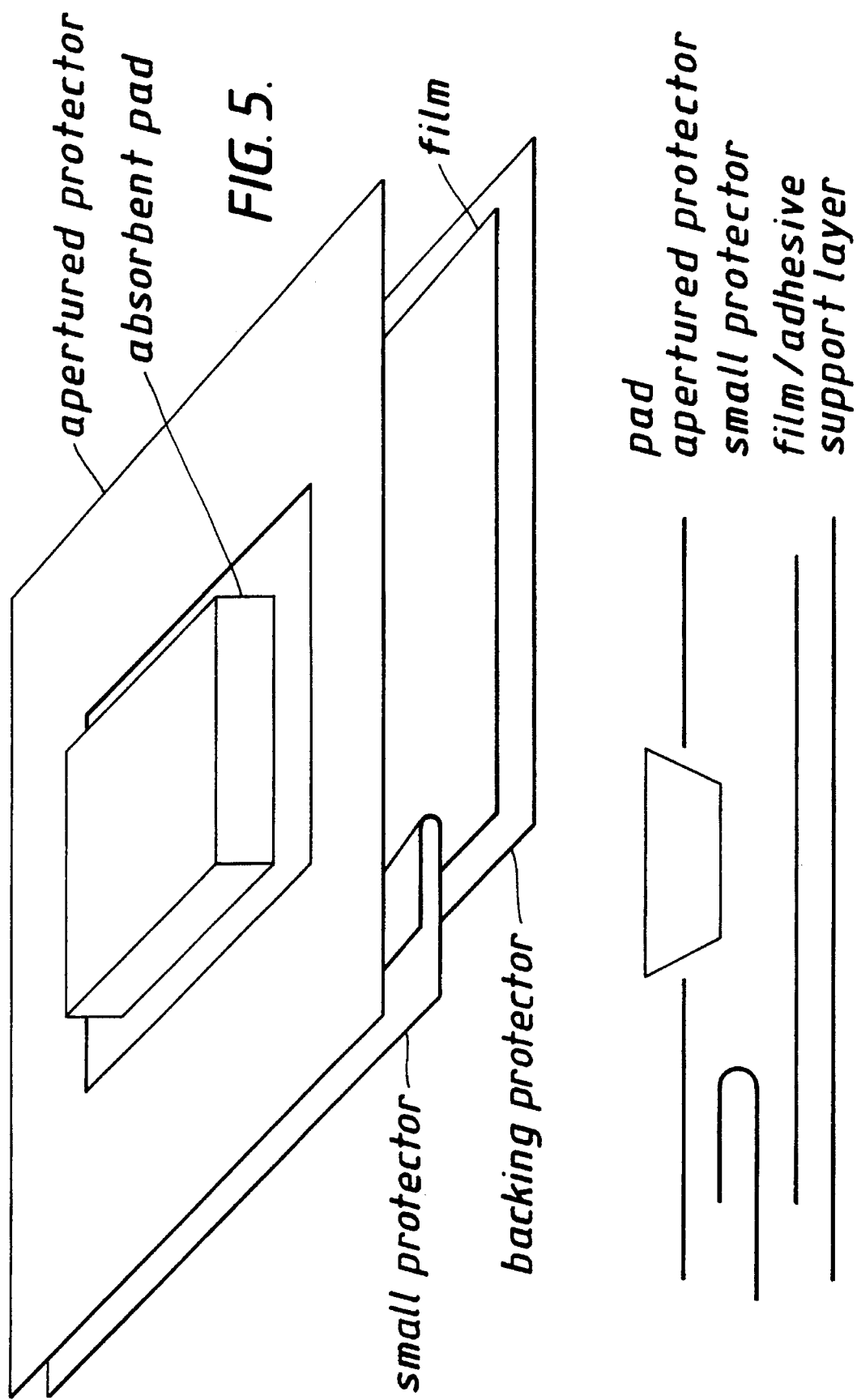
FIG. 5 is a schematic representation of a dressing provided with an apertured protector.

In use, the protector (11) is removed and the pad (8) placed upon a wound. In the embodiment of FIG. 3 the dressing is held by the smaller protector (12). The backing layer (2) is then adhered to the skin around the site of the wound.

Following adhesion to the skin the support layer (4) may be removed.

We claim:

1. An adhesive dressing comprising a water vapor permeable, liquid water and bacteria impermeable backing layer having a pressure sensitive adhesive layer over one surface thereof and coextensive therewith, a pad adhered to a portion of the adhesive layer, a removable protector which covers the remainder of the adhesive layer, and a conformable support layer which is removably attached to the non-adhesive surface of the backing layer, said removable protector being provided with an aperture through which the pad is adhered to the adhesive layer.

2. An adhesive dressing according to claim 1 wherein the size of the aperture is less than the surface of the pad such that the pad partially overlies the surface of the protector.

3. An adhesive dressing according to claim 2 wherein the extent to which the pad overlaps the surface of the protector is up to 25% of the width of the pad.

4. An adhesive dressing according to claim 2 wherein the backing layer comprises polyurethane film.

5. An adhesive dressing according to claim 4 wherein the backing layer comprises a hydrophilic polyurethane.

6. An adhesive dressing according to claim 2 wherein the backing layer has a moisture vapour transmission rate of at least 500 $gm^{-2}$ 24 $hr^{-1}$ at 37° C. at 100% to 10% relative humidity difference.

7. An adhesive dressing according to claim 2 wherein the backing layer has a thickness of from 15 to 100 µm.

8. An adhesive dressing according to claim 2 wherein the pad comprises a polyurethane foam.

9. An adhesive dressing according to claim 2 wherein the removable protector is divided into two or more pieces or is fenestrated to facilitate removal.

10. An adhesive dressing according to claim 2 wherein the removable protector extends beyond the backing layer at one or more edges and comprises first and second parts, the first part having a portion extending away from the adhesive surface and bent back to form a v-shape and the second part having a portion extending away from the adhesive and overlying the v-shaped first part.

11. An adhesive dressing according to claim 2 wherein the support layer extends beyond the backing layer on one or more sides.

12. A method of manufacturing an adhesive dressing comprising a water vapor permeable, liquid water and bacteria impermeable backing layer having a pressure sensitive adhesive layer over one surface thereof and coextensive therewith, a pad adhered to a first portion of the adhesive layer, a removable protector which covers the remainder of the adhesive layer, and a conformable support layer which is removably attached to the non-adhesive surface of the backing layer, said removable protector being provided with an aperture through which the pad is adhered to the adhesive layer, said method comprising:

casting a solution of a polymer which is to form the backing layer onto a long strip of a film which is to form the support layer;

casting or transfer coating an adhesive layer onto the backing layer such that the adhesive layer is coextensive with the backing layer;

applying a pad to said first portion of the adhesive layer; and applying a removable protector to the adhesive layer in one or two pieces such that the removable protector covers the remainder of said adhesive layer.

13. A method of treating a wound or indwelling catheter site which comprises applying thereto an adhesive dressing comprising a water vapor permeable, liquid water and bacteria impermeable backing layer having a pressure sensitive adhesive layer over one surface thereof and coextensive therewith, a pad adhered to a portion of the adhesive layer, a removable protector which covers the remainder of the adhesive layer, and a conformable support layer which is removably attached to the non-adhesive surface of the backing layer, said removable protector being provided with an aperture through which the pad is adhered to the adhesive layer, said method comprising removing the removable protector, applying the adhesive layer to the skin, and then removing the support layer.

14. An adhesive dressing according to claim 2, wherein the stripping load of the support layer from the backing layer is greater than that of the protector from the adhesive layer and wherein the peeling strength between the support layer and the backing layer is such that, in use, on removal of the support layer from the backing layer, the backing layer is not dislodged from the skin.

15. An adhesive dressing according to claim 1 wherein the adhesive-bearing backing layer is sufficiently thin that it is subject to excessive wrinkling unless handled with extreme care.

* * * * *